US006794536B1

(12) United States Patent
Shinal

(10) Patent No.: US 6,794,536 B1
(45) Date of Patent: Sep. 21, 2004

(54) METHOD FOR PREPARATION OF DISODIUM PAMIDRONATE

(75) Inventor: Edward C. Shinal, Holmdel, NJ (US)

(73) Assignee: Aesqen, Inc., Priceton, NJ (US)

( * ) Notice: Subject to any disclaimer, the term of this patent is extended or adjusted under 35 U.S.C. 154(b) by 763 days.

(21) Appl. No.: 09/456,460

(22) Filed: Dec. 8, 1999

Related U.S. Application Data

(63) Continuation-in-part of application No. 09/414,401, filed on Oct. 7, 1999, now abandoned, which is a continuation-in-part of application No. 09/209,153, filed on Dec. 10, 1998, now Pat. No. 6,160,165.

(51) Int. Cl.$^7$ .................................................. C07F 9/38
(52) U.S. Cl. ...................................................... 562/17
(58) Field of Search ................................... 562/16, 17

(56) References Cited

U.S. PATENT DOCUMENTS

| | | | | |
|---|---|---|---|---|
| 3,962,432 | A | 6/1976 | Schmidt-Dünker | 424/204 |
| 4,142,916 | A | 3/1979 | Ogasa et al. | 127/63 |
| 4,304,734 | A | 12/1981 | Jary et al. | 260/502.5 |
| 4,327,039 | A | 4/1982 | Blum et al. | 260/502.5 |
| 4,336,243 | A | 6/1982 | Sanvordeker et al. | 424/28 |
| 4,439,194 | A | 3/1984 | Harwood et al. | 604/890 |
| 4,513,891 | A | * 4/1985 | Hain et al. | 222/213 |
| 4,639,338 | A | 1/1987 | Stahl et al. | 260/502.5 |
| 4,680,416 | A | * 7/1987 | Hokanson et al. | 549/292 |
| 4,711,880 | A | * 12/1987 | Stahl et al. | 514/108 |
| 4,797,388 | A | 1/1989 | Francis | 514/23 |
| 4,814,326 | A | 3/1989 | Rosini et al. | 514/108 |
| 4,816,259 | A | * 3/1989 | Matthews et al. | 424/463 |
| 4,922,007 | A | 5/1990 | Kieczykowski et al. | 562/13 |
| 5,096,717 | A | 3/1992 | Wirth et al. | 424/490 |
| 5,139,786 | A | 8/1992 | Ferrini et al. | 424/449 |
| 5,159,108 | A | 10/1992 | Kieczykowski | 562/13 |
| 5,296,475 | A | 3/1994 | Flesch et al. | 514/108 |
| 5,344,825 | A | 9/1994 | Khanna et al. | 514/108 |
| 5,366,965 | A | 11/1994 | Strein | 514/102 |
| 5,403,829 | A | 4/1995 | Lehtinen et al. | 514/102 |
| 5,431,920 | A | 7/1995 | Bechard | 424/480 |
| 5,449,819 | A | 9/1995 | Venkataramani et al. | 562/13 |
| 5,569,466 | A | 10/1996 | Tanner et al. | 424/452 |
| 5,650,165 | A | 7/1997 | Akemi et al. | 424/448 |
| 5,780,055 | A | 7/1998 | Habib et al. | 424/464 |
| 5,785,985 | A | 7/1998 | Czech et al. | 424/448 |
| 5,888,550 | A | 3/1999 | Cook et al. | 424/490 |
| 5,932,240 | A | 8/1999 | D'Angelo et al. | 424/449 |
| 6,057,306 | A | * 5/2000 | Wilson et al. | 514/102 |

FOREIGN PATENT DOCUMENTS

| | | | |
|---|---|---|---|
| CN | 1144806 A | 3/1997 | C07F/9/38 |
| DE | 19820974 | 5/1998 | C07F/9/38 |
| EP | 0177443 | 8/1984 | C07F/9/38 |
| EP | 0600834 | 11/1992 | A61K/31/66 |
| WO | WO-96/05842 | 2/1996 | A61K/31/685 |

OTHER PUBLICATIONS

Journal of Chromatography A by Quitasol et al 671 pp 273–279, Sep. 1994.*
Merriam Webster's Collegiate Dictionary 10th edition, Editor Fredrick Mish, 1993.*
Physicians' Desk Reference (Handbook) editor R Arky edition 52 publisher Medical Economics Company Inc st Montvale New Jersey pp 1823–1828, Nov. 1997.*
CA 123:1319687 abs of Int J Pharm 123(2) my Nicklin pp 187–197, 1995.*
CA75:40273 abs of Cron. Farm. by Cooper et al 14(1) pp 19–27, 1971.*
"Product Information Section", *Physicians' Desk Reference*, *52nd Ed.*, pp. 1824–1828, (1998).
Su, G., et al., "Preparation of amino–diphosphinic acid and its sodium salts as bone absorption inhibitors", *Chemical Abstracts*, vol. 128, No. 10, Abstract No. 115081, (Mar. 9, 1998).
Cooper, J., "Quality Control of Plastic Pharmaceutical Containers", *Cron. Farm. 14*(1), 19–27, (1971).
Nicklin, P.L., et al., "Development of a minimun–calcium Caco–2 monolayer model: calcium and magnesium ions retard the transport of pamidronate", *International Journal of Pharmaceutics*, vol. 123, No. 2 (Sep. 12, 1995) pp. 187–197.
In: *Angewandte Biopharmazie (Applied Biopharmacy)*, Chap. 19, Ritschel, W., (ed.), Stuggart, Germany, 2 p., (1973).
In: *Bentley's Textbook of Pharmaceuticals, Eighth Edition*, Rawlins, E. A., (ed.), Bailliere Tindall, London, p. 186–194, (1977).
Huettenrauch, R., et al., "Effect of Adsorption Layers on Liquid Absorption by Powders", *Pharmazie (Germany)*, 26, Abstract from CAPLUS, Document No. 75:91517, 1 p., (1971).

* cited by examiner

*Primary Examiner*—Jean F. Vollano
(74) *Attorney, Agent, or Firm*—Schwegman, Lundberg, Woessner & Kluth, P.A.

(57) ABSTRACT

The invention provides a method of preparing anhydrous disodium pamidronate or an aqueous disodium pamidronate solution for pharmaceutical use.

4 Claims, No Drawings

METHOD FOR PREPARATION OF DISODIUM PAMIDRONATE

This application is a continuation-in-part of U.S. patent application Ser. No. 09/414,401, filed Oct. 7, 1999 now abandoned which is a continuation-in-part of U.S. patent application Ser. No. 09/209,153, filed Dec. 10, 1998 now U.S. Pat. No. 6,160,165.

BACKGROUND OF THE INVENTION

Disodium 3-amino-1-hydroxypropane-1,1-diphosphonate or "disodium pamidronate" has the formula:

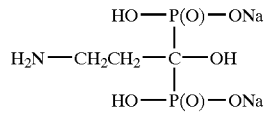

It is commercially available as the lyophilized pentahydrate, under the name AREDIA® from Novartis Pharmaceuticals Corp., and is used to inhibit bone resorption, i.e., to treat moderate or severe hypercalcemia associated with malignancy, with or without bone metastases. The preparation of the crystalline pentahydrate from pamidronic acid is disclosed by Stahl et al. in U.S. Pat. Nos. 4,711,880 and 4,639,338. This material is prepared by partially neutralizing a heated slurry of pamidronic acid with aqueous sodium hydroxide (NaOH) to pH 7–7.5 and then initiating crystallization at ≧50° C. The mixture is slowly cooled to 0–5° C. and the disodium pamidronate is collected by filtration. This product is described as having "excellent crystallinity" and as being "completely stable to storage under approximately normal ambient conditions." It comprises about 24.1–25% water.

The crystalline product ("Modification E") is contrasted with an amorphous product disclosed to be prepared by the general process of Jary et al. (U.S. Pat. No. 4,304,734). In Comparison Example 1 of the '338 patent, pamidronic acid is neutralized to pH 7.4 with aqueous NaOH and the reaction mixture is concentrated to dryness under reduced pressure at 60–70° C. and then dried at 20 mbar to constant weight. However, the amorphous product that is obtained is described as deliquescent in air, contains 12.9% of retained water and, as taught in the '338 patent, will convert to the pentahydrate. Stahl et al. also teach the interconversion of other crystalline forms of disodium pamidronate depending upon humidity and amount of water present, which demonstrates the difficulty in utilizing preformed disodium salts of pamidronic acid for further processing into sterile pharmaceutical dosage forms.

Thus, a need exists for a simple method to prepare disodium pamidronate and dosage forms thereof that are stable to storage and suitable for reconstitution and/or intravenous infusion/injection.

SUMMARY OF THE INVENTION

The present invention provides a pharmaceutical unit dosage form comprising an aqueous solution of disodium pamidronate enclosed in a suitable container, such as an ampule or vial, under an inert atmosphere. Preferably the container is designed for "single use". Preferably, the container is formed of a material that does not contain calcium in a form that can be sequestered by the dissolved disodium pamidronate.

The present invention also provides a method for the preparation of amorphous, essentially anhydrous (≦1–2 wt-% water) disodium pamidronate (the "product"). This solid product can be stored under nitrogen at otherwise ambient conditions, and readily reconstituted with sterile water or physiological salt solutions for injection or infusion into a patient in need of treatment therewith.

The present method also comprises a method to make an aqueous solution of disodium pamidronate by addition of aqueous sodium hydroxide to a stirred slurry of pamidronic acid in an about 2:1 molar ratio of NaOH to acid, optionally comprising excess mannitol, to yield a clear solution of pH 6.5±0.1. Aqueous phosphoric acid is added as needed if the pH following NaOH addition is too high. A small amount of aqueous NaOH can be added if the pH is too low. Preferably, 1 N aqueous NaOH is used.

The solution is frozen and lyophilized under reduced pressure to yield amorphous, essentially anhydrous disodium pamidronate. The product is stable when stored under dry nitrogen at otherwise ambient conditions. Preferably, the about pH 6.5 solution is filtered and aliquots are introduced into suitable container(s), then frozen (−25 to −40° C.), lyophilized (10–25 mbar, 20–40° C.) in situ, and the containers sealed under positive nitrogen pressure to yield a plurality of unit dosage forms of solid disodium pamidronate, optionally in admixture with mannitol.

For example, vials containing 30 mg, 60 mg and 90 mg of sterile lyophilized disodium pamidronate, each optionally containing 470 mg, 400 mg, and 375 mg of mannitol can readily be prepared and utilized as disclosed in *Physician's Desk Reference* (52d ed., 1988) at pages 1824–1828.

The present invention further provides an improved method for the preparation of aqueous solutions and dosage forms of disodium pamidronate of defined composition, using pamidronic acid as a starting compound and titrating an aqueous pamidronic acid slurry having a concentration of about 0.1 to 0.5 M, preferably about 0.130 to about 0.135 M, to visual clarity at a pH of approximately 6.5 using aqueous sodium hydroxide (NaOH) or other suitable base to yield an aqueous solution of disodium pamidronate. Preferably, an about 2:1 molar ratio of NaOH or other metal hydroxide to pamidronic acid is used. Mannitol is an optional component of the slurry, preferably present in a molar excess to pamidronate as in the solutions described above, prior to lyophilization. Alternately, the solution is titrated to clarity using aqueous sodium hydroxide and the final pH adjusted to approximately 6.5±0.1 using phosphoric acid as needed. The clear aqueous solution of disodium pamidronate is then filtered and packaged as unit dosage forms comprising aliquots of the filtered solution.

This aspect of the present invention entirely eliminates the generation and isolation of various metastable, hydrated, crystalline and/or amorphous physical forms of disodium pamidronate (each of which can interchange with the other, depending upon the circumstance of available moisture or temperature in the substance environment). The present invention affords stable pamidronate compositions which can be stored at temperatures of, for example, 0° C. or less (frozen), about 2 to about 8° C. (refrigerated), or about 20 to about 30° C. (room temperature). The compositions can be used to prepare dosage forms suitable for therapeutic oral, rectal, transdermal, intranasal, or intravenous administration.

As used herein, the term "about" incorporates inherent variability of the parameter referenced, due to measurement techniques known to the art, i.e., pH, or water content (loss on drying).

DETAILED DESCRIPTION OF THE INVENTION

The present invention provides an improved method for the preparation of stable unit dosage forms of disodium pamidronate having constant composition. Pamidronic acid is used as a starting compound, from which an aqueous pamidronic acid slurry (the slurry being at least partially opaque) is formed. The concentration of pamidronic acid in the slurry is about 0.1 to 0.5 M, preferably about 0.130 to about 0.135 M. The pamidronic acid slurry is titrated to visual clarity, at a pH of approximately 6.5±0.1, using aqueous sodium hydroxide (NaOH) or other suitable base to yield a solution of disodium pamidronate. Mannitol is an optional component of the slurry, and is preferably present in molar excess to the pamidronic acid. Alternately, the solution can be titrated to clarity using aqueous NaOH and the final pH can be adjusted to approximately 6.25–6.75 using phosphoric acid as needed.

The clear aqueous solution formed can be filtered and packaged as one or more unit dosage forms comprising aliquots of the filtered solution. The filtered solution can also be further processed by freezing, for example, at approximately −25 to −40° C. and lyophilizing at 10–25 mbar at 20–40° C. in situ to yield amorphous, essentially anhydrous ($\leqq$1–2 wt % water) disodium pamidronate which can be stored under nitrogen and readily reconstituted with sterile water or physiological salt solution for injection or infusion into a patient in need thereof. The invention described herein eliminates the need for the formation of metastable hydrates, which results in a dosage form of more constant composition than those described by Jary et al. (U.S. Pat. No. 4,304,734) and Stahl et al. (U.S. Pat. Nos. 4,711,880 and 4,639,338).

The solution of the present invention is used to prepare separately packaged oral or intravenous unit dosage forms. Unit dosage forms can comprise pamidronate solution prepared by the method of the present invention and packaged into pharmaceutical vials or ampules. Preferably, the containers are "single use" in that they contain one unit dosage form and are not reclosable. Also, it is preferably the employ container components that free of calcium ($Ca^{+2}$) that can be sequestered by the pamidronate solution. Alternately, pamidronate solutions prepared by the method of the present invention can be used to prepare dosage forms such as, for example, soft gelatin capsules, transdermal patches, intranasal sprays, rectal suppositories, or enteric-coated capsules.

Unit dosage forms can also comprise disodium pamidronate solution prepared by the method of the present invention wherein pamidronate is bound to one or more ion exchange resins. These compositions can be administered as, for example, liquid formulations or as sustained release dosage forms using polymer coatings known to those of skill in the art.

For intravenous administration, disodium pamidronate prepared by the method of the present invention can be packaged into vials or ampules comprising from 5 to 20 ml of the pamidronate solution, wherein the disodium pamidronate is present at a concentration of, for example, approximately 3 mg/ml to about 9 mg/ml. Prior to administration, disodium pamidronate solution within a vial or ampule is removed and diluted using an appropriate volume of a calcium-free solution such as a 0.9% w/v sodium chloride (normal saline) or a 5% dextrose solution.

For oral administration, capsule dosage forms can be prepared from anhydrous disodium pamidronate or from a disodium pamidronate solution prepared by the method of the present invention. Methods for preparing pharmaceutical formulations in capsule form are known to those of skill in the art. For example, one such method has been described in U.S. Pat. No. 5,569,466 (Tanner et al.), which describes the preparation of fill compositions for soft gelatin capsules.

Enteric coating compositions are also known to those of skill in the art. Enteric coatings are described, for example, in U.S. Pat. No. 5,888,550 (Cook et al.), which describes cellulose acetate phthalate enteric coating compositions. With proper selection of polymer coatings, such as an acrylic-based resin designed to dissolve at a pH above 7, delivery to the distal ileum and colon can be achieved. An example of such an acrylic-based resin is the Eudragit® E-3 (acrylate ester copolymer) series (Rohm-Haas, Philadelphia, Pa.).

U.S. Pat. No. 5,780,055 (Habib et al.) describes beads of microcrystalline cellulose and a disintegrant for delivery of easy-to-swallow pharmaceutical compositions. U.S. Pat. No. 5,431,920 (Bechard et al.) describes a double-coated bimodal release form of bisphosphonic acid for administration to subjects exhibiting upper gastrointestinal tract sensitivity to bisphosphonic acid compounds. See, also, Strein (U.S. Pat. No. 5,366,965). These methods, for example, can be used to prepare dosage forms of the disodium pamidronate solution of the present invention for administration to patients who, for example, have difficulty swallowing capsules or who exhibit gastric sensitivity to disodium pamidronate.

Methods for preparing suppository formulations are known to those of skill in the art and can be used to prepare suppository dosage forms comprising a disodium pamidronate or a disodium pamidronate solution in admixture with ingredients such as those described in U.S. Pat. No. 4,439,194 (Harwood, et al.), which describes a water and drug delivery system for suppository use.

For intradermal delivery, transdermal patches can be formed using disodium pamidronate or a disodium pamidronate solution prepared by the method of the present invention. Methods for producing transdermal patches to deliver therapeutic compositions are described, for example, in U.S. Pat. No. 5,932,240 (D'Angelo et al.), U.S. Pat. No. 4,336,243 (Sanvordeker et al.), and U.S. Pat. No. 5,650,165 (Akemi et al.). A transdermal patch or percutaneous absorption preparation can be held in contact with the skin by a pressure-sensitive adhesive. Examples of suitable pressure-sensitive adhesives include silicone pressure-sensitive adhesives and polyisobutylene pressure-sensitive adhesives, which are known to those of skill in the art. A pressure-sensitive adhesive suitable for use in forming a transdermal patch for disodium pamidronate delivery is described, for example, in U.S. Pat. No. 5,785,985 (Czech et al.).

Formulations for intranasal delivery comprise, for example, nasal drops or sprays having a pamidronate concentration of approximately 3 mg/ml to about 30 mg/ml of carrier matrix. The invention will be further described by reference to the following detailed example.

EXAMPLE 1

Preparation of Disodium Pamidronate

For a batch size of 5 L, 587.5 g (3.2 moles) of mannitol is dissolved in 3.5 L of water. Pamidronic acid (31.6 g, 0.133 moles) is mixed with a 1.0 L aliquot of the mannitol solution to form a slurry. The slurry is then transferred into the remainder of the mannitol solution, and stirred for at least 15 min. Aqueous 1 N sodium hydroxide (270 ml) is then added and the mixture is stirred until a clear, colorless solution results. The pH is then adjusted to 6.5±0.1 using either 1 M aqueous phosphoric acid or 1 N aqueous sodium hydroxide, as needed. The solution is then filtered through a 0.22 micron filter, and filled at 20° C. into vials at 4.0 ml (4.172 g)/vial, under sterile conditions. The aqueous solution is frozen at −37° C. and lyophilized (20 mbar, 20–40° C.) to yield 1,250 vials, each containing 30 mg of amorphous disodium pamidronate. The vials are sealed under positive nitrogen pressure. The disodium pamidronate is amorphous (noncrystalline) by X-ray diffraction and contains 0.7 wt-% water (USP 23 <731>).

EXAMPLE 2

Preparation of Disodium Pamidronate

For a batch size of 5 L, 587.5 g (3.2 moles) of mannitol is dissolved in 3.5 L of water. Pamidronic acid (31.6 g, 0.133 moles) is mixed with a 1.0 L aliquot of the mannitol solution to form a slurry. The slurry is transferred into the remainder of the mannitol solution, and stirred for about 15 min. Aqueous 1 N sodium hydroxide (270 ml) is added and the mixture is stirred until a clear, colorless solution results. The pH is adjusted to 6.5±0.1 using either 1 M aqueous phosphoric acid or 1 N aqueous sodium hydroxide, as needed. The solution is filtered through a 0.22 micron filter, and filled at 20° C. into glass vials at 4.0 ml (4.172 g)/vial, and the vials are sealed in the lyophilizer in an inert atmosphere under sterile conditions.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for preparing a packaged therapeutic aqueous disodium pamidronate solution comprising:

(a) preparing a slurry of pamidronic acid in water;

(b) combining aqueous sodium hydroxide with said slurry in an about 2:1 molar ratio of sodium hydroxide to pamidronic acid; to yield a solution of disodium pamidronate having visual clarity and a pH of about 6.5; and (c) packaging at least one liquid unit dosage of said solution in a sealed ampule or vial.

2. The method of claim 1 wherein the slurry includes an effective stabilizing amount of mannitol.

3. The method of claim 1 or 2 wherein the solution is packaged under an inert atmosphere.

4. The method of claim 1 or 2 wherein the vial or ampule is free of $Ca^{+2}$ that can be sequestered by disodium pamidronate.

* * * * *

UNITED STATES PATENT AND TRADEMARK OFFICE
CERTIFICATE OF CORRECTION

PATENT NO. : 6,794,536 B1
DATED : September 21, 2004
INVENTOR(S) : Shinal

It is certified that error appears in the above-identified patent and that said Letters Patent is hereby corrected as shown below:

Title page,
Item [73], Assignee, delete "Priceton" and insert -- Princeton --, therefor.
Item [56], References Cited, OTHER PUBLICATIONS,
"CA75:40273" reference, delete "my" and insert -- by --, therefor.
"Nicklin" reference, delete "minimun" and insert -- minimum --, therefor.

Signed and Sealed this

Fifteenth Day of February, 2005

JON W. DUDAS
*Director of the United States Patent and Trademark Office*